(12) United States Patent
Dash et al.

(10) Patent No.: US 12,622,594 B2
(45) Date of Patent: May 12, 2026

(54) SYSTEM FOR DETECTION OF BREAST CANCER MARGIN AND METHOD THEREOF

(71) Applicants: TERALUMEN SOLUTIONS PRIVATE LIMITED, Chennai (IN); ADIUVO DIAGNOSTICS PRIVATE LIMITED, Nellore (IN)

(72) Inventors: Jyotirmayee Dash, Chennai (IN); Shaumik Ray, Chennai (IN); BalaSubrahmanyam Pesala, Chennai (IN); Geethanjali Radhakrishnan, Chennai (IN)

(73) Assignees: TERALUMEN SOLUTIONS PRIVATE LIMITED, Chennai (IN); ADIUVO DIAGNOSTICS PRIVATE LIMITED, Nellore (IN)

( * ) Notice: Subject to any disclaimer, the term of this patent is extended or adjusted under 35 U.S.C. 154(b) by 362 days.

(21) Appl. No.: 18/394,950

(22) Filed: Dec. 22, 2023

(65) Prior Publication Data

US 2024/0122493 A1 Apr. 18, 2024

Related U.S. Application Data

(63) Continuation of application No. PCT/IN2022/050571, filed on Jun. 22, 2022.

(30) Foreign Application Priority Data

Jun. 23, 2021 (IN) .............................. 202141012592

(51) Int. Cl.
*A61B 5/05* (2021.01)
*A61B 5/00* (2006.01)
*A61B 5/0507* (2021.01)

(52) U.S. Cl.
CPC .......... *A61B 5/0507* (2013.01); *A61B 5/0071* (2013.01); *A61B 5/7425* (2013.01); *A61B 5/743* (2013.01)

(58) Field of Classification Search
CPC ... A61B 5/0507; A61B 5/0071; A61B 5/7425; A61B 5/743
See application file for complete search history.

(56) References Cited

U.S. PATENT DOCUMENTS

| | | | | |
|---|---|---|---|---|
| 2010/0160774 A1* | 6/2010 | Dabiri | .................. | A61B 5/0073 600/425 |
| 2016/0354494 A1* | 12/2016 | Gazendam | .............. | A61L 27/34 |
| 2023/0113897 A1* | 4/2023 | Deliwala | ............ | G01N 21/8806 356/317 |

FOREIGN PATENT DOCUMENTS

| | | |
|---|---|---|
| CN | 112004459 A | 11/2020 |
| IN | 202111029059 A | 8/2021 |

OTHER PUBLICATIONS

Carver et al., "Real Time Detection of Breast Cancer at the Cellular Level," *Journal of Cellular Physiology* 234(5), May 2019. (14 pages).
Examination Report, mailed Jan. 30, 2023, for Indian Application No. 202141012592. (7 pages).
International Search Report and Written Opinion, mailed Sep. 16, 2022, for Indian Application No. PCT/IN2022/050571. (11 pages).

(Continued)

*Primary Examiner* — Nicole M Ippolito
(74) *Attorney, Agent, or Firm* — Seed Intellectual Property Law Group LLP

(57) ABSTRACT

The disclosure discloses a multispectral imaging system and method for real time detection of breast cancer margin during a tumor resection surgery by combining terahertz and autofluorescence images. The system comprises terahertz and fluorescence modules in a housing having a sample holder to enable raster scan of the sample. The terahertz module has terahertz emitter antennas for generating terahertz radiation to the sample, and a terahertz detector to receive reflected terahertz signal from the sample. A fluo- (Continued)

rescence module with UV excitation LEDs induces fluorescence and a camera to receive emitted autofluorescence. A microcontroller connected to an electronic control unit is configured to display or to overlap and combine terahertz and autofluorescence images to determine breast cancer margin, via an AI module. The AI module is configured to perform classification of the feature set machine learning models to obtain classification with high with high sensitivity and specificity.

8 Claims, 8 Drawing Sheets

(56) References Cited

OTHER PUBLICATIONS

Nichols et al., "Miniature spectral imaging device for Wide-field quantitative functional Imaging of the Morphological Landscape of Breast Tumor Margins," *Journal of Biomedical Optics* 22(2), Feb. 2017. (17 pages).

Rodriguez-Ruiz et al., "Stand-Alone Artificial Intelligence for Breast Cancer Detection in Mammography: Comparison With 101 Radiologists," *Journal of the National Cancer Institute* 111(9): 916-922, Sep. 2019.

Smith et al., "Real-time, Intraoperative Detection of Residual Breast Cancer in Lumpectomy Cavity Walls Using a Novel Cathepsin-Activated Fluorescent Imaging System," *Breast Cancer Research and Treatment* 171(2), Sep. 2018. (14 pages).

* cited by examiner

FIG. 2B                                    FIG. 2C

SYSTEM FOR DETECTION OF BREAST CANCER MARGIN AND METHOD THEREOF

BACKGROUND

Technical Field

The present disclosure relates to the detection of breast cancer margin and a system to detect the breast cancer margins. More particularly, the present disclosure relates to the detection of breast cancer margin after the removal of tumor or cancerous cells via surgery by employing Terahertz and Fluorescence radiations and spectroscopic analysis along with Artificial Intelligence based system.

Description of the Related Art

Breast cancer is one of the major causes of cancer related deaths across the world, especially in India and other developing nations. Breast cancer accounts for 14% of cancers in Indian women. Both in rural and urban India, the number of breast cancer cases have been seen to be on the rise. A 2018 report of Breast Cancer statistics recorded more than 1.6 lakh newly registered cases and 0.87 lakh reported deaths. Post cancer survival for women with breast cancer was reported 60% for Indian women, as compared to 80% in the U.S.

The main reason for the higher mortality rate in India and other developing nations is the lack of proper infrastructure for effective diagnosis, delayed and incorrect cancer margin detection. The low survival rates can be addressed by accurate and timely detection of cancer margin which will also potentially reduce the requirement for repeat breast conservation surgeries. Breast conserving surgery (BCS) is an effective treatment for early-stage cancers as long as the margins of the respected tissue are free of disease according to consensus guidelines for patient management. 11 to 23% of patients undergo breast conservation surgery (BCS) in India instead of radical mastectomy (60 to 70% in western countries). BCS provides better cosmetic outcome, better psychological adjustment, less cost and better recovery. However, 20% of BCS cases fail due to inaccurate margin detection which means recurrence of cancer is more and there is a need of repeat surgery. However, 15% to 35% of patients undergo a second surgery since malignant cells are found close to or at the margins of the original resection specimen.

The current gold standard technique for determination breast cancer margin is histopathology assessment which requires chemical staining and 2-7 days of time and analysis by a trained pathologist. Further to histopathology, two handheld probes, viz., the Margin Probe, developed by Dune Medical, Israel and ClearEdge, developed by LsBioPath, U.S.A. have been effectively employed for detection of breast cancer margin. Both these devices employ the same core method of determining tissue electrical properties, and thus malignancy, based on reflected wavelengths. However, it also has serious drawbacks of low sensitivity and specificity iKnife is another potential device based on rapid evaporative ionization mass spectrometry (REIMS) which has high sensitivity and specificity but is minimally invasive.

At present, there are no diagnostic devices in India which can be employed for intraoperative assessment of breast cancer margin.

The current gold standard technique is histopathology assessment which assesses the microscopic cellular structure of the tissue. These approaches are slower than other imaging techniques and usually more labor intensive and require surgical pathologists. In this process, the tissue will be fixed, processed, sectioned, stained with hematoxylin and eosin (H&E), and interpreted microscopically. Although the approach is accurate, it is also time-consuming and is completed over several days (5 to 7 days).

Frozen sectioning is the most commonly used method for intraoperative margin assessment during surgery. Frozen section analysis consists of freezing small pieces of tissue, then sectioning, staining, and interpreting them under a microscope. The time between the tissue leaving the operating room (OR) and a microscopic diagnosis is more than one hour. The disadvantage of freezing tissue is that it generates significant artifacts, especially in fatty tissues, such as the breast. It can also be damaging such that tissue used for frozen sectioning may not be viable for the routine histopathologic margin assessment performed later. Frozen section interpretations are expensive and require additional technical staff to cut the specimens. These limitations result in a small fraction of the specimen margin being frozen and analyzed, leaving a large percentage of the tissue unassessed.

Moreover, most of the smaller hospitals and multi-specialty clinics could not afford frozen section analysis. In these hospitals, patients have to wait for 3 to 7 days for histopathology results. Hence, a system/device is needed for intraoperative detection of the cancer margin rapidly with high specificity by conserving maximum normal tissue.

Hence, there is a need of a device which can detect the breast cancer margin during surgical procedures of tumor removal and accurately detect breast cancer margin in non-invasive method with minimum skills.

Present disclosure intends to use multispectral technique to accurately detect breast cancer margin during the operative process which can reduce the need for reoperations as well as potentially decrease mortality rates. Terahertz and autofluorescence technologies may be used as complementary tools for detection of structural, pathological and metabolic changes respectively due to cancer progression. Artificial Intelligence (AI) algorithms may be used for improving the accuracy and efficiency of diagnosis of breast cancer margin.

Objects of the Disclosure

The primary object of the present disclosure is to provide a compact, cost-effective, non-invasive, rapid device and system for detection of breast cancer margin by using multispectral techniques for assessing cancer margin in real time during the surgery.

Yet another object of the present disclosure is to provide device for detection of breast cancer margin and by employing terahertz and fluorescence in a non-invasive manner along with artificial intelligence for accurate detection of breast cancer margin during the surgery.

Still another object of the present disclosure is to provide a device to capture the reflected intensity of terahertz signals from cancerous tissues and normal tissues.

Another object of the present disclosure is to provide a device and system to detect variation/alteration in fluorescence properties with respect to fluorescence of ordinary tissue.

Yet another object of the present disclosure is to provide a device and a system to provide accurate THz intensity and corresponding absorption coefficient and refractive indices from the tissue samples and difference in fluorescence of both the tissue types.

Still another object of the present disclosure is to provide a device and system for detection of breast cancer margin having improved accuracy, sensitivity and specificity with the help of artificial intelligence-based system which combines terahertz and fluorescence data.

Yet another object of the present disclosure is to provide a device and system for the detection of breast cancer margin by measuring two spectral properties such as Terahertz and fluorescence simultaneously in order to perform the assessment of cancer margins in real time.

BRIEF SUMMARY

In one aspect of the disclosure, a compact, cost-effective, non-invasive, rapid and robust diagnostic device for detection of breast cancer margin during intraoperative surgery using multispectral techniques in real time is disclosed. The device of the present disclosure includes plurality of spectral modules selected from terahertz and fluorescence module in a non invasive manner coupled with artificial intelligence system for the accurate detection of the breast cancer margin during the intraoperative procedures. Said device comprises a Housing (14) to accommodate various optical components of Terahertz and fluorescence module means for generating, guiding and determining emitted radiation from the tissue sample. The device is electrically coupled with electronic control unit, receives DC supply from electronic control unit and optical input from optical controller to control various optical components therein and microcontroller enabled electronic device for processing, resizing and determining cancer margin with 85-90% specificity.

In another aspect of the disclosure, a non-invasive, rapid and robust system for detection of breast cancer margin during intraoperative surgery using multispectral techniques in real time is disclosed. Said system comprises; a Housing accommodating terahertz module and Fluorescence module for emitting, guiding and detecting the terahertz and fluorescence spectra respectively passing through tissue sample, a Sample holder arranged behind the first end of said Housing to place a tissue sample excised by a surgeon during breast cancer surgery is mounted on a two axis Stepper motor in such a way that sample holder moves in Z-axis and X-axis along with Stepper motor for carrying out faster and accurate scanning of tissue sample automatically, an Optical controller powered by DC supply, to provide optical input to the optical parts in the Housing, an Electronic control unit for converting AC power supply to DC power supply and providing the DC power supply to said Optical controller and a Microcontroller configured with AI module for effective spectroscopic feature extraction, image processing and specific determination of breast cancer margin intraoperatively.

The disclosure further discloses a method of detection of breast cancer margin in real time using multispectral technique and AI module.

BRIEF DESCRIPTION OF THE SEVERAL VIEWS OF THE DRAWINGS

FIGS. 2B and 2C show servo gears for movement of emission filter.

FIG. 6A shows hematoxylin and eosin (H&E) stained pathology image, FIG. 6B shows cancer region identified bright in H&E image, FIG. 6C shows non-cancer region in bright, FIG. 6D shows terahertz image of the same sample. FIG. 6E shows H&E image resized to THz image, FIG. 6F shows overlapping of H&E image and THz image, FIG. 6G and FIG. 6H show cancer and non-cancer regions identified from THz image.

FIG. 7A shows hematoxylin and eosin (H&E) stained pathology image, FIG. 7B shows cancer region identified bright in H&E image, FIG. 7C shows non-cancer region in bright, FIG. 7D shows fluorescence image of the same sample. FIG. 7E shows H&E image resized to fluorescence image, FIG. 7F shows overlapping of H&E image and fluorescence image, FIG. 7G and FIG. 7H show cancer and non-cancer regions identified from fluorescence image.

FIG. 8A shows results of classification using THz image, FIG. 8B shows results of classification using fluorescence image and FIG. 8C shows classification results by AI model using combined images of THz and fluorescence.

Figures 1A, 1B, 1C:
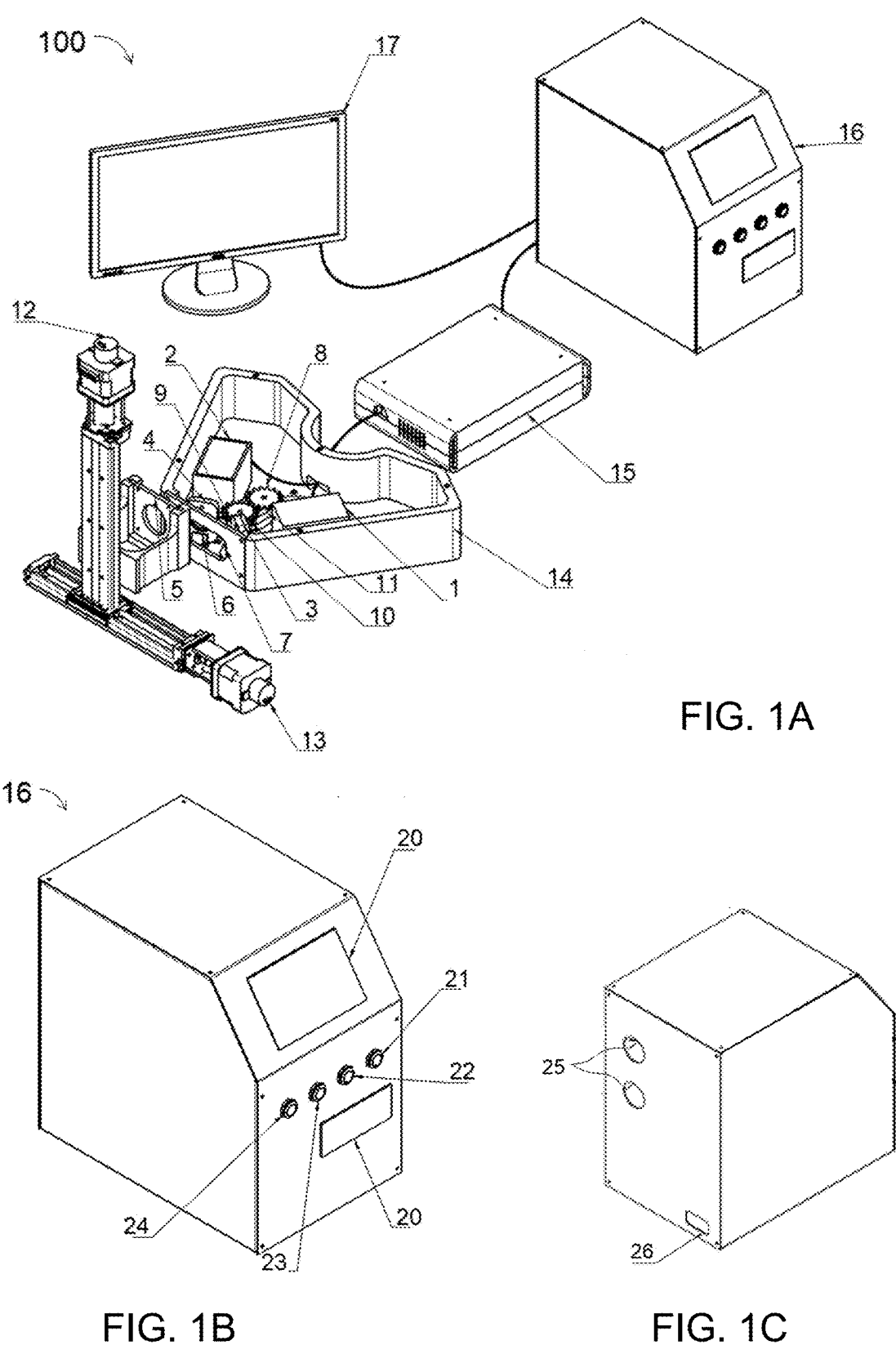
FIG. 1A shows the system of detection of breast cancer margin of the present disclosure.
FIG. 1B shows components of the control unit and FIG. 1C shows rear of control unit.

Following table describes the legends used in the drawings and their description

| Sr. No. | Legend | Legend Description |
|---------|--------|-------------------|
| 1 | Terahertz Emitter | Terahertz transmitter (antenna) to generate Terahertz radiation |
| 2 | Terahertz Detector | Terahertz receiver (antenna) to detect Terahertz radiation |
| 3 | TPX Lens 1 | Polymethylpentene (TPX) lens to collimate/focus Terahertz radiation emitted from Terahertz transmitter |
| 4 | TPX Lens 2 | Polymethylpentene (TPX) lens to guide Terahertz beam to the detector |
| 5 | Sample holder | Sample holder to place tissue sample |
| 6 | Excitation LED 1 | Fluorescence Source to generate radiation in the infrared/ultraviolet range for fluorescence modules |
| 7 | Excitation LED 2 | Fluorescence Source to generate radiation in the infrared/ultraviolet range for fluorescence modules |
| 8 | Servo Gear | for movement of emission filter |
| 9 | Camera | To capture fluorescence image |
| 10 | Emission Filter | |
| 11 | Servo Motor | |
| 12 | Z-stage of the stepper motor | For carrying out faster scanning of the sample automatically in Z axis |
| 13 | X-stage of the stepper motor | For carrying out faster scanning of the sample automatically in X axis |
| 14 | Housing | For accommodating Terahertz and Fluorescence components |
| 15 | Optical Controller | |
| 16 | Electronic Control Unit | |

-continued

| Sr. No. | Legend | Legend Description |
|---------|--------|--------------------|
| 17 | Microcontroller | For recording imaging and spectroscopic results and data analysis |
| 18 | Optical input bias | To the housing for generating Terahertz radiation |
| 19 | Terahertz radiation emitted from housing | |
| 20 | LCD display | For displaying signals acquired from housing |
| 21 | Power switch | |
| 22 | Function generator switch | |
| 23 | Laser controller switch 1 | |
| 24 | Laser controller switch 2 | |
| 25 | Fans | |
| 26 | Electrical AC supply | |

DETAILED DESCRIPTION

The disclosure relates to a system and device for detection of accurate breast cancer margin by using multispectral techniques with non-ionizing radiation which may be able to detect breast cancer margin with high specificity and sensitivity. This disclosure employs Terahertz combined with Fluorescence technologies along with artificial intelligence algorithms to provide a cost effective rapid, real time intraoperative detection of breast cancer margin.

The device for real time intra operative detection of breast cancer margin using multispectral techniques with high specificity and sensitivity wherein; said multi spectral technique is a combination of terahertz radiation and auto-fluorescence.

FIG. 1 discloses a system for breast cancer margin detection of the present disclosure. The system comprises; a Housing (14) narrow at its first end with increasing diameter at second end having a semicircular inwardly curved portion in the middle of second end which is exposing to an Optical controller (15) having opening for emitting terahertz and fluorescence spectra, wherein said Housing (14) accommodating terahertz module and Fluorescence module for emitting, guiding and detecting the terahertz and fluorescence spectra respectively passing through tissue sample, a Sample holder (5) arranged behind the first end of said Housing (14) to place a tissue sample excised by a surgeon during breast cancer surgery is mounted on a two axis Stepper motor (12, 13) in such a way that sample holder (5) moves in Z-axis and X-axis along with Stepper motor (12,13) for carrying out faster and accurate scanning of tissue sample automatically, an Optical controller (15) powered by DC supply, to provide optical input to the optical parts in the Housing (14), an Electronic control unit (16) for converting AC power supply to DC power supply and providing the DC power supply to said Optical controller (15) and a Microcontroller (17) configured with AI module for effective spectroscopic feature extraction, image processing and specific determination of breast cancer margin intraoperatively.

Figure 3:
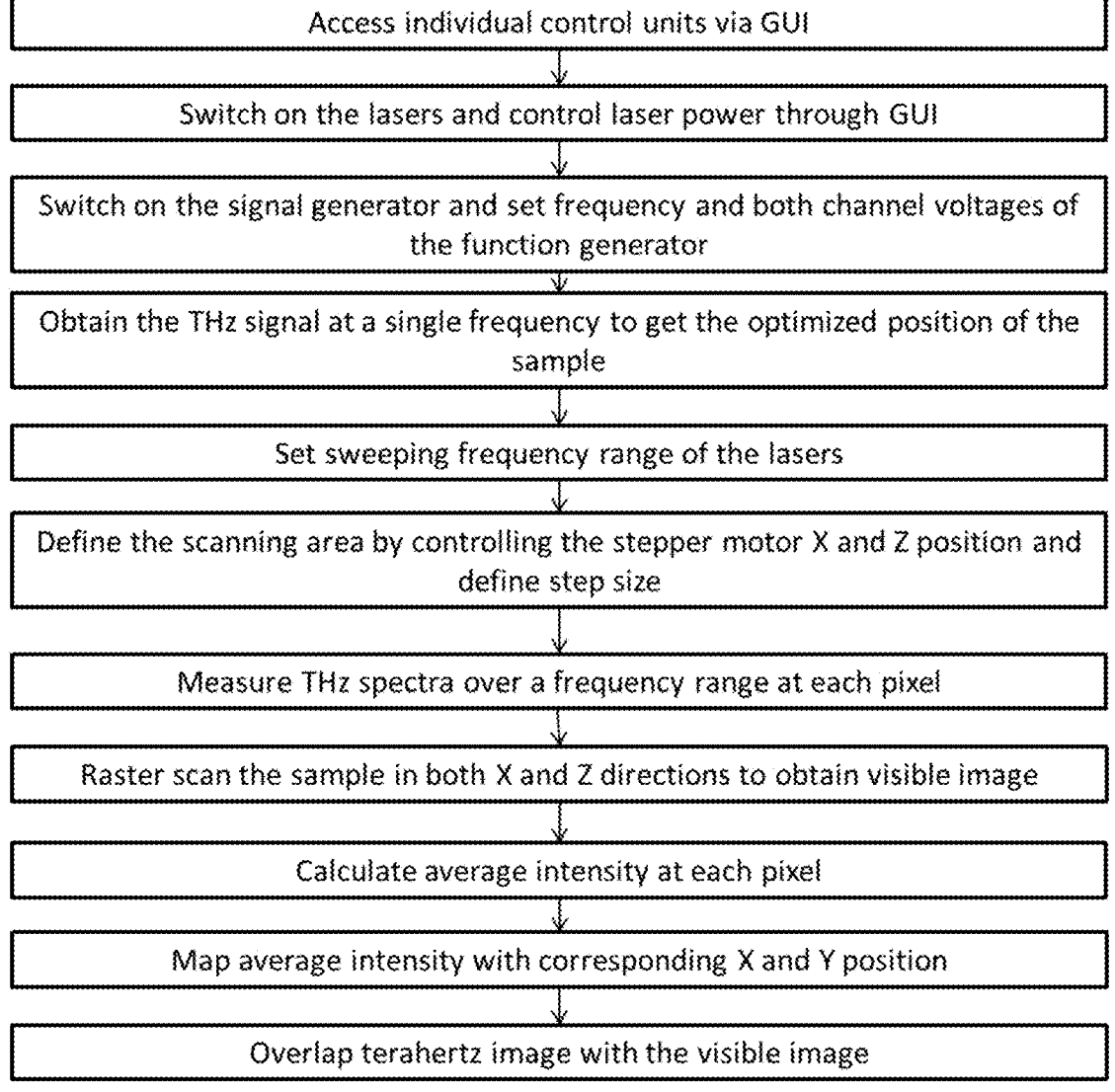
FIG. 3 shows the block diagram of Terahertz module emitting terahertz radiations from cancerous tissue samples.

In one embodiment, the disclosure relates to a system for intraoperative detection of breast cancer margin comprising; a Housing (14) accommodating Terahertz and Fluorescence modules; wherein said Terahertz module further comprises of; two or more Terahertz antennas (1,2) for generating terahertz radiation and receiving terahertz radiation after passing through tissue sample, one or more Terahertz Plano convex lens (TPX lens) (3,4) for focusing/guiding terahertz radiations emitted from one of the antennas (1,2). Block diagram of Terahertz module emitting the cancerous tissue samples is shown in FIG. 3

In one embodiment, the disclosure relates to a system for intraoperative detection of breast cancer margin comprising; a Housing (14) accommodating Terahertz and Fluorescence modules; wherein said Fluorescence module further comprises of; Fluorescence imaging module, image acquisition module, an image processing module, display module and control system.

Figure 4:
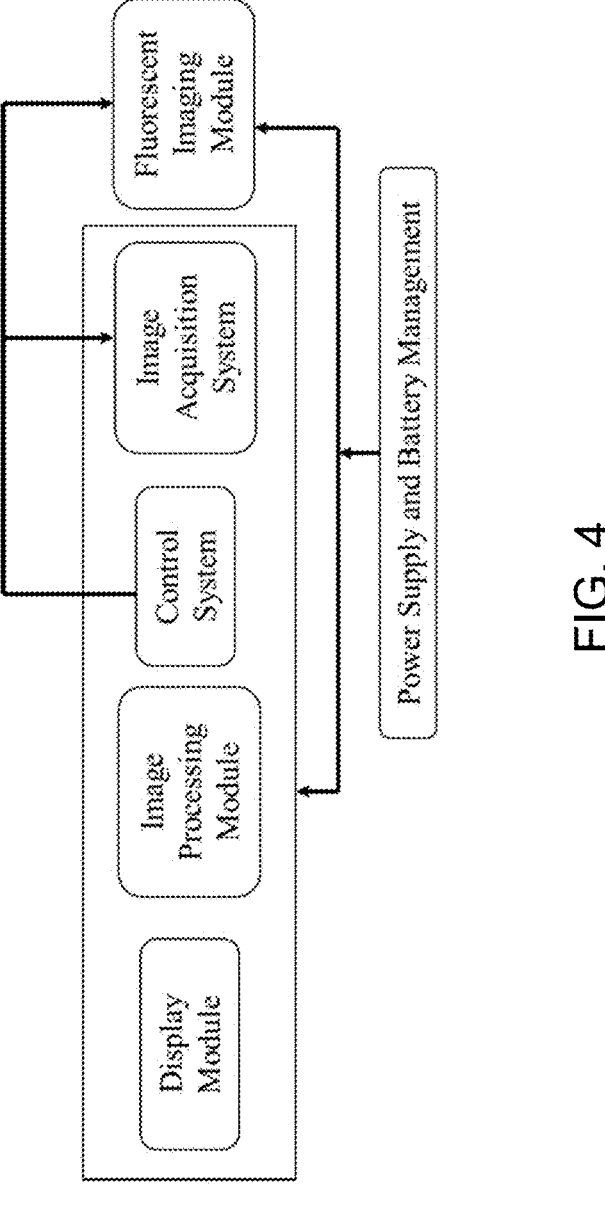
FIG. 4 shows the block diagram of Fluorescence module capturing autofluorescence from cancerous tissue samples.

Block diagram of fluorescence module for capturing autofluroscence from cancerous tissue samples is shown in FIG. 4.

The Fluorescence Imaging Module comprises one or more multiwavelength UV excitation LEDs (6, 7) to generate radiation in the infrared/ultraviolet range, one or more emission filters (10) of predetermined wavelength to filter the emitted fluorescence radiation by tissue sample, a servo gear (8) and a nano servo motor (11) for the movement of said emission filters (10) and a CMOS camera (9) for fluorescence image acquisition. The whole module is controlled by the control system configured on Microcontroller (17) based electronic device such as PC, laptop etc. which sets excitation/emission wavelength in a sequence and captures a multispectral image of the tissue and analyses the same.

In another embodiment of the present disclosure, a system for intraoperative detection of breast cancer margin wherein; the Optical controller (15) houses temperature tunable lasers and laser diode drivers for tuning the lasers. The Optical controller (15) is supplied by DC supply. The output from the optical control unit would be utilized to provide optical input to the Terahertz antennas (1,2) placed in the Housing (14) to generate Terahertz radiation.

In yet another embodiment of the present disclosure, a system for intraoperative detection of breast cancer margin wherein; said Electronic control unit (16) further comprise AC power supply (26) converting AC power supply to DC power supply and passing the same to Optical controller (15). It is used to provide bias to the Terahertz antennas (1,2). The Electronic control unit (16) also comprises data acquisition unit for capturing Terahertz radiations, LCD displays (20) may display the Terahertz signal and acquired Terahertz images from the tissue sample. In various embodiments, the electronic control unit may include a board for data acquisition, function generator to provide bias to the terahertz emitter (1). In various embodiments, a lock-in-amplifier is provided to amplify the terahertz signal. Terahertz intensity measured from the lock-in amplifier may be fed to a computer for displaying the image. In various embodiments, a power distribution board may be provided to supply power to the electronic control unit. Various switches such as Function generator switch (22), Laser controller switch 1(23), Laser controller switch 2 (24) may be provided to control the operations of components. Fans (25) are provided to control the temperature of the microcontroller.

In another embodiment of the present disclosure, a system for intraoperative detection of breast cancer margin comprising; wherein said AI Module comprises a smart machine learning algorithm for differentiation of breast cancer and normal tissues on Terahertz and fluorescence imaging. Effective spectroscopic feature extraction and classification methods are highly desired to distinguish the THz signals of different tissues. In this disclosure, Principal Component Analysis (PCA) is used as an important feature extraction method followed by Machine Learning algorithms, such as support vector machine (SVM) and Random Forest analysis.

For acquisition of data and real time imaging, a graphical user interface (GUI) may be developed to display the images obtained from the device on the microcontroller enabled device (17). This may help the doctors to take the decision accurately and immediately during the surgery.

Present disclosure provides a system which is completely non-invasive and reagent free technology. The system may help the oncosurgeons to analyze the cancer margin much rapidly and help to differentiate the cancer and non-cancer tissues based on their structural difference, metabolic changes and the water content.

Present disclosure provides a non-invasive and reagent free system for intraoperative detection of breast cancer margin with high sensitivity and specificity which detects the cancer margin within 40-60 minutes simultaneously during the surgery and thus provides rapid detection techniques.

Advantages of Terahertz Radiation

Terahertz radiation is highly sensitive to polar substances, such as water. Hence, compared to X-rays, THz waves can provide better contrast in the case of soft tissues. Physiological changes related to tumor in tissues result in increased water content and decreased lipid concentration in comparison with normal tissues. Hence, the reflected Terahertz signal provides contrast between the cancerous and normal tissues based on the water and lipid concentration.

Terahertz technology can also be effectively employed to extract optical parameters. Due to the physical and biochemical changes in the tumor tissue, the dielectric properties change and may involve alteration in the optical coefficients. Hence, the Terahertz reflected spectra changes in the tumor tissue compared to normal tissues. Parameters that are sensitive to change in the Terahertz spectra are extracted and used to differentiate tumor from adjacent normal tissue.

Imaging of the biological tissues may be carried out over a short span of Terahertz frequencies and the differentiation between the cancerous and normal tissues is done based on the variation in reflected Terahertz signal from the cancerous tissues and the adjacent normal tissues, which is shown as image contrast.

The developed Continuous Wave THz system demonstrates the capability of real-time imaging applications for breast cancer margin detection.

Autofluroscence technology may determine distinct fluorescence responses of cancerous tissues compared to normal tissues. Since, no fluorescent dye is used, the brightness and contrast of the autofluroscence images obtained from breast tissue are low, and the color information is not rich.

Figure 2A:
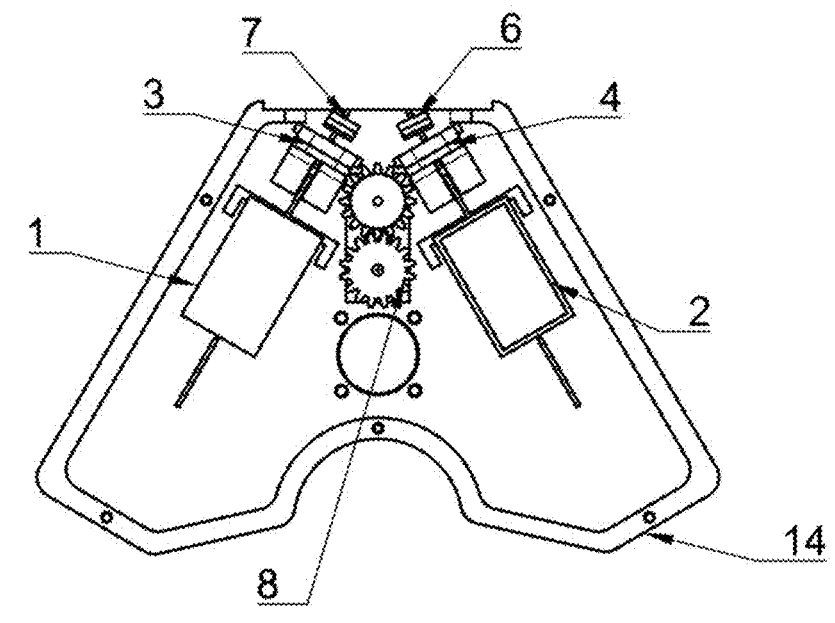
FIG. 2A shows the device housing with terahertz transmission and receiver units, along with lenses.
Figure 2D:
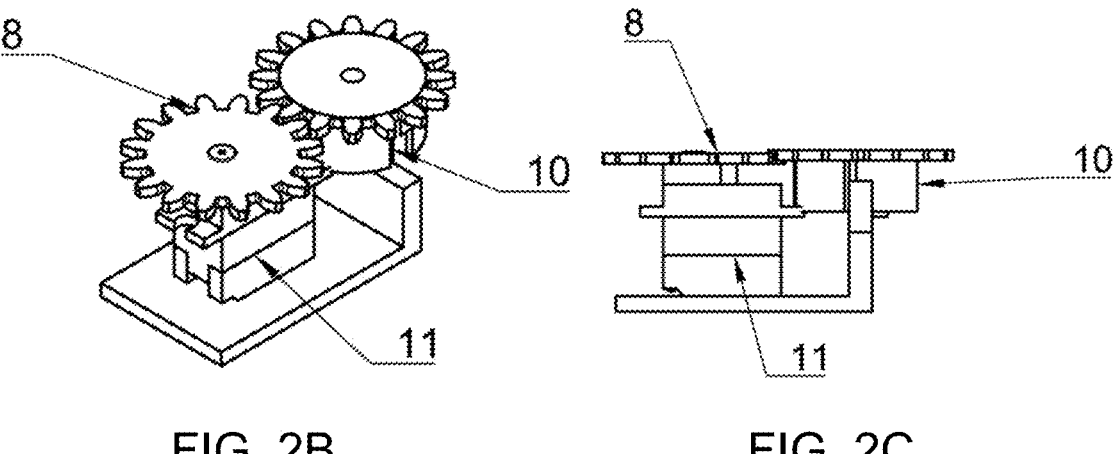
FIG. 2D shows camera to capture fluorescence image.
Figure 2D:
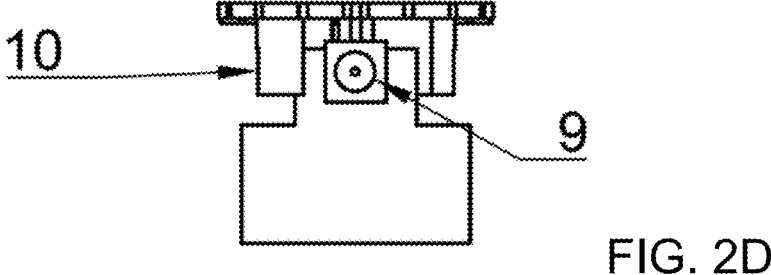

FIG. 2 describes a device for real time intra operative detection of breast cancer margin using multispectral techniques with high specificity and sensitivity. Figure also explains different components of the device shown as separate parts for better description. Said device comprises; a Housing (14) narrow at its first end which is exposed to sample holder (5) for passing radiation through sample and increasing diameter at second end having a semicircular inwardly curved portion in the middle of second end which is exposing to an Optical controller (15) having opening for emitting terahertz and fluorescence spectra wherein; said Housing (14) accommodating, Terahertz module means for generating Terahertz radiation, passing through the tissue sample and detecting the emitted radiation through the tissue sample, wherein; said Terahertz module further comprises of; two or more Terahertz antennas (1,2) for generating terahertz radiation and receiving terahertz radiation passing through tissue sample respectively, one or more terahertz Plano convex lens (TPX lens) (3,4) for focusing/guiding terahertz radiations emitted from two of the antennas (1,2), and Fluorescence module means for generating fluorescence radiation, passing through tissue sample and detecting the emitted radiation, said Fluorescence module further comprises of; one or more multiwavelength UV excitation LEDs (6,7) to generate radiation in the infrared/ultraviolet range along with the driver board, one or more emission filters (10) of predetermined wavelength to filter the emitted fluorescence radiation by tissue sample, a servo gear (8) and a nano servo motor (11) for the movement of said emission filters (10) and a CMOS camera (9) for image acquisition, a sample holder (5) for holding a tissue sample excised from a patient's body during surgery is mounted on a two axis stepper motor moving in X-axis and Z-axis direction (12, 13) for rapid scanning and automatic movement.

The device for real time intra operative detection of breast cancer margin using multispectral techniques with high specificity and sensitivity, further electronically connected with an Optical controller (15) which provides DC supply to Optical components in said Housing (14) and to an Electronic control unit (16) which further comprises, data acquisition unit for capturing Terahertz radiations, LCD displays (20) displays the Terahertz signal and acquired Terahertz images from the tissue sample. Various switches such as Function generator switch (22), Laser controller switch 1(23), Laser controller switch 2 (24) and Fans (25) are provided to control individual units housed therein.

Said device is rapid, non-invasive, reagent free and can be effectively used for detection of breast cancer margin with high specificity and sensitivity based on the variation in Terahertz intensity of the reflected THz signals from the cancerous tissues and normal tissues due to the different water content in the tissues.

The present disclosure utilizes a light source with a wavelength span of 300-500 nm may be employed. An RGB camera may be employed as a detector along with an optical filter wheel to allow the radiation with a particular wavelength (300 to 750 nm) to be received using the camera.

Figure 5:
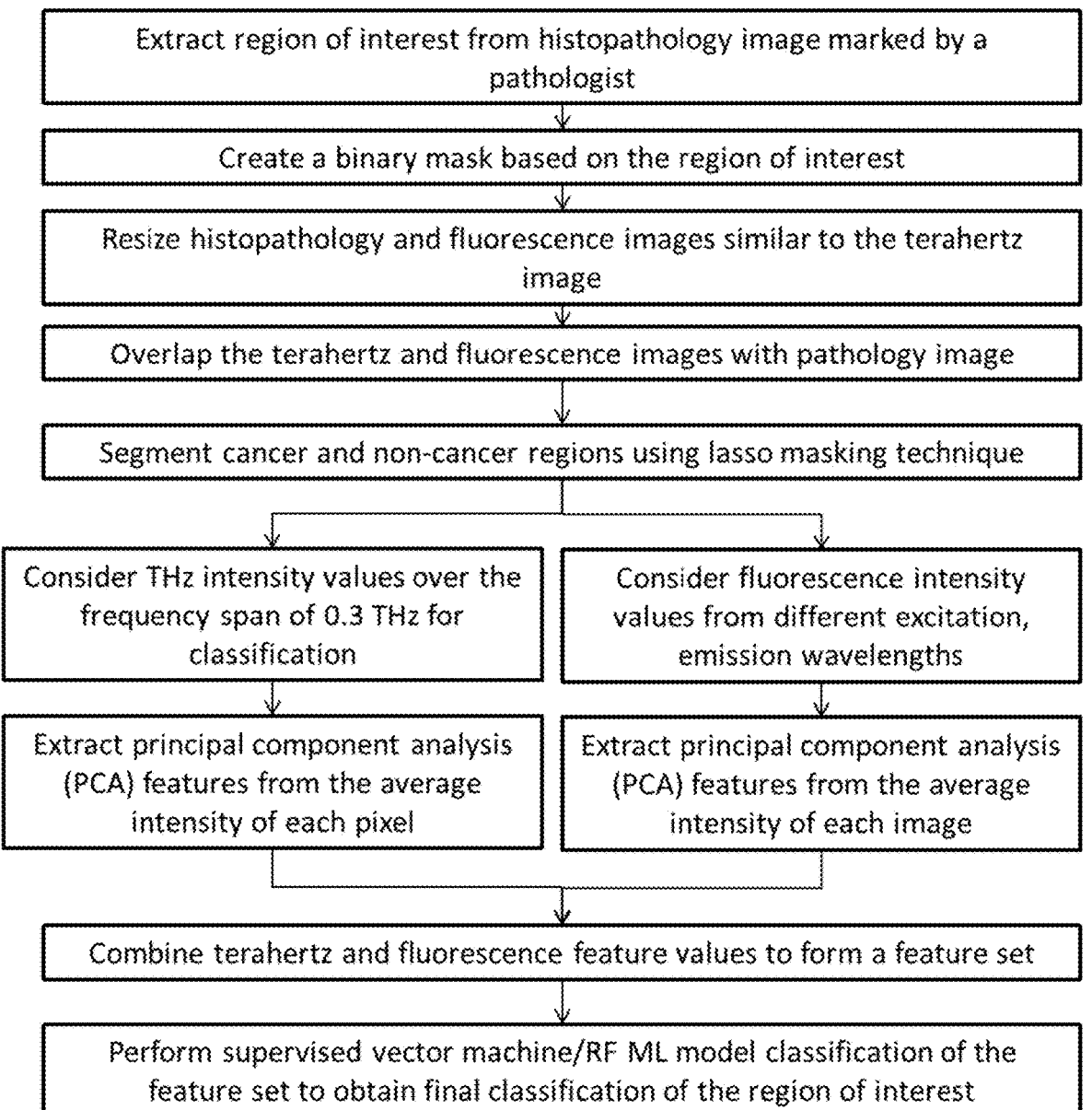
FIG. 5 shows logical process flow of AI module of the system for detection of breast cancer margins of the present disclosure.
Figures 6A, 6B, 6C, 6D, 6E, 6F, 6G, 6H:
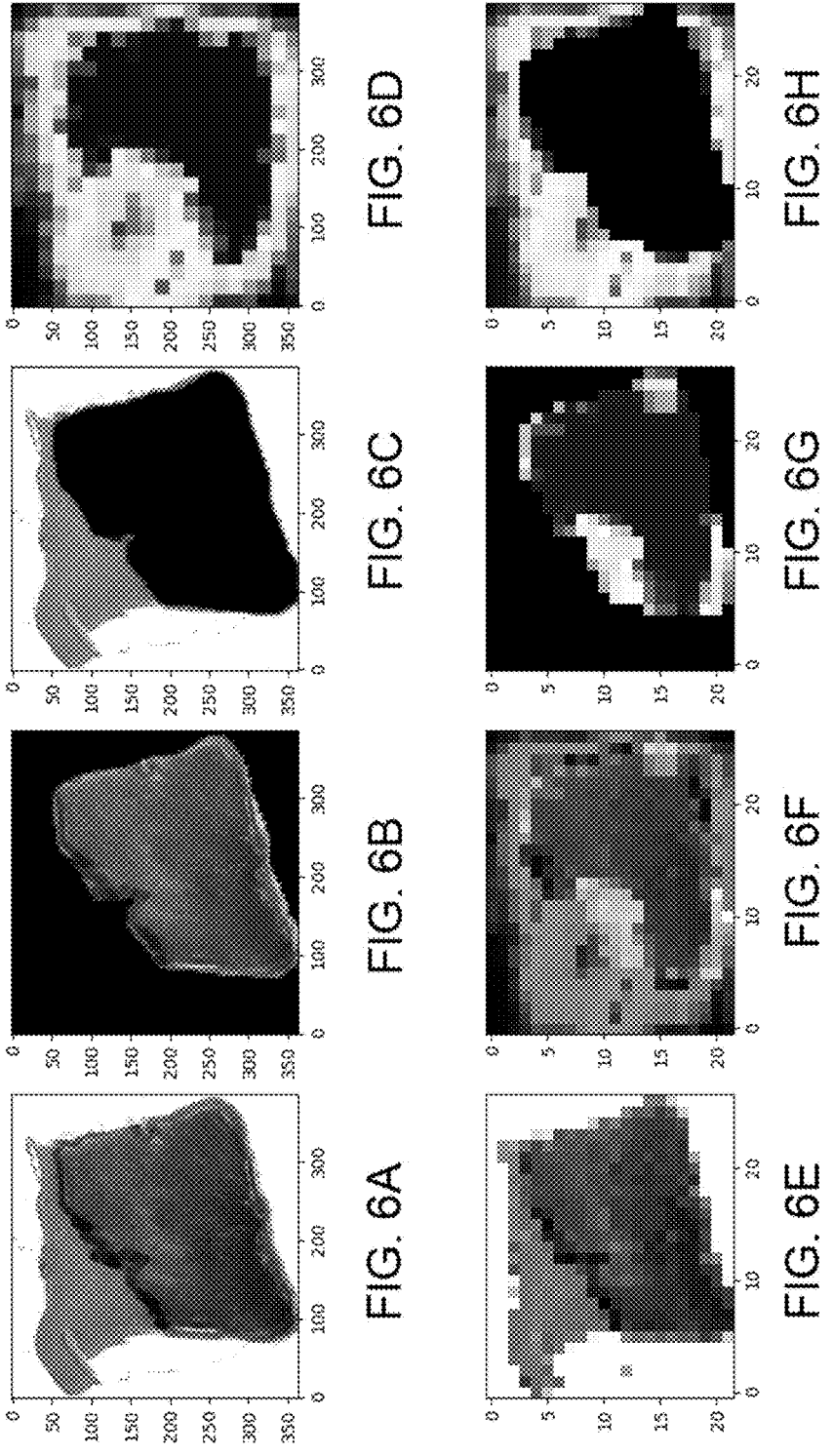
FIG. 6A-6H show the separation of cancer and non-cancer region in Terahertz Image.
Figures 7A, 7B, 7C, 7D, 7E, 7F, 7G, 7H:
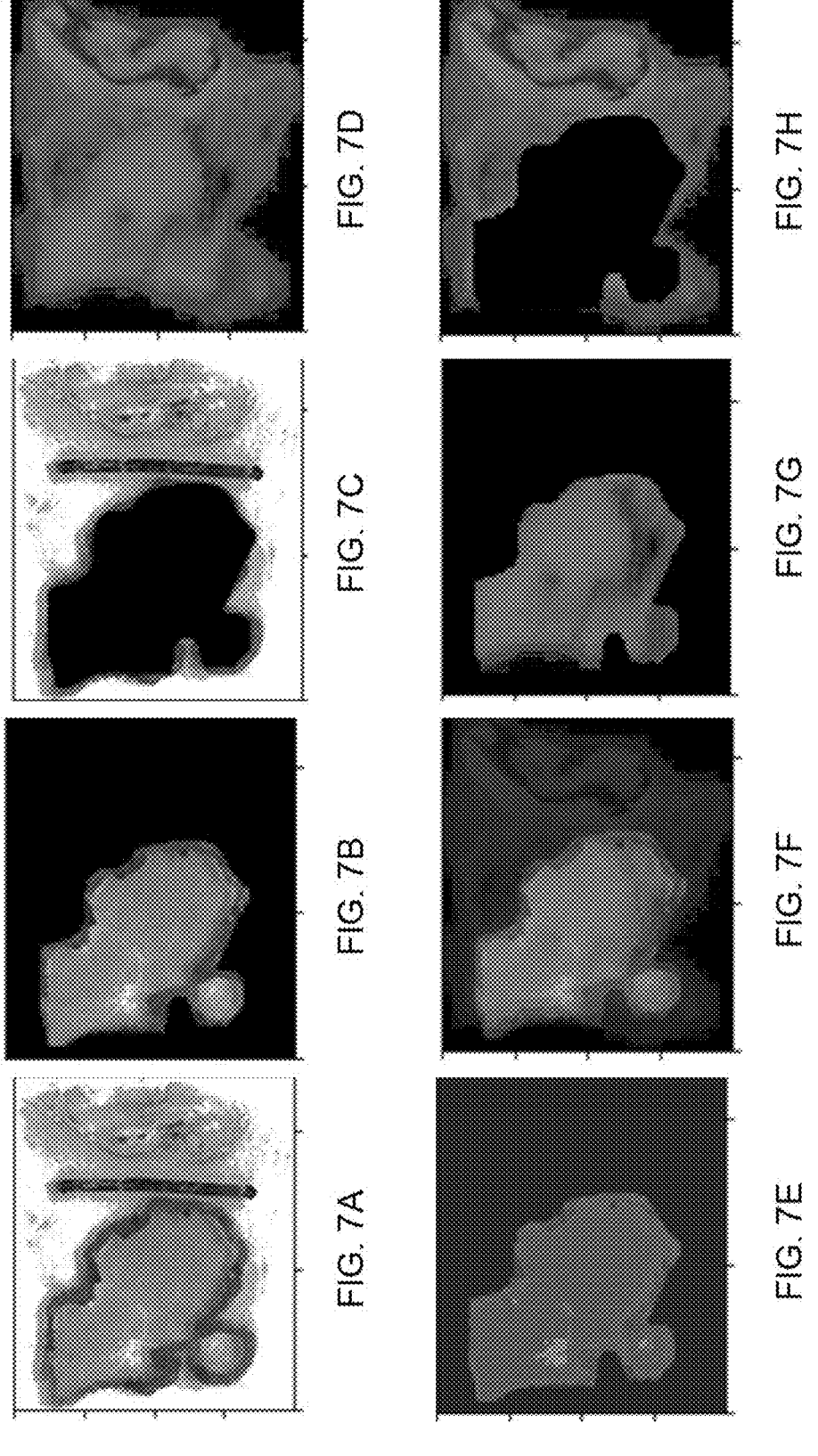
FIG. 7A-7H show differentiation of tumor and non-tumor tissue in the fluorescence images by overlapping the mask of H&E slide.

FIG. 5 depicts the method of accurately determining the breast cancer margin of the present disclosure using multispectral technique using AI module. The AI module is configured at the microcontroller (17) based electronic device such as laptop, smart phone, PC, tablet etc. capable of performing the functions as per block diagram mentioned in FIG. 5.

In another embodiment of present disclosure, the disclosure relates to a method for detection of breast cancer margin using multispectral technique and AI module rapidly and intraoperatively in real time. Said method comprising the steps of; removing the tissue samples by the oncosurgeons during cancer surgery, treating the tissue samples with required reagents as per standard protocol of tissue culture, mounting the treated tissue on sample holder (5), passing the Terahertz radiation through the sample, obtaining emitted Terahertz radiation from each pixel of the tissue sample by Terahertz detector (2), passing the fluorescence radiation through the tissue sample, capturing the autofluroscence image by camera (9), dissemble the tissue from the sample holder (5) to hand over to the pathologist for obtaining histopathology images, processing the spectral images (Terahertz and Autofluroscence) by graphical user interface configured in Microcontroller enabled device (17), combining terahertz & autofluroscence image results, resizing comparing with histopathological images, segmenting cancer & non-cancer region, classifying and determining the breast cancer margin with high sensitivity and specificity by AI module.

Compared to conventional Terahertz or fluorescence spectrometers which can measure individual data separately, the developed device may assist to measure both the spectral properties simultaneously. Hence, this may help the clinicians to take the decisions of margin assessment more accurately with significantly reduced time. This may also provide additional information compared to traditional spectrometers and may help in early detection and timely treatment of cancer.

EXAMPLES

Materials and Methods

Sample Preparation:

The tissues samples are obtained from biorepository, Rajiv Gandhi Cancer Institute and Research Centre after clearing institutional ethical clearance. The formalin fixed paraffin embedded (FFPE) tissues are prepared as per standard protocol. Once tumor and non-tumor tissues are excised, the tissues were fixed in formalin and embedded in paraffin. Also, standard hematoxylin and eosin (H&E) stained pathology slides of 4 to 5 µm were cut from the same blocks in order to provide the histopathology images for the purpose of validation. Tissue samples with separate tumor tissues, non-tumor tissues and tumor tissues with adjacent normal tissues are measured using fluorescence and Terahertz imaging.

Results:

Terahertz Imaging Results:

Although FFPE blocks are completely dehydrated, the contrast in the THz intensity between the benign and malignant tissues is observed, mainly due to the structural differences between the samples.

For more extensive validation of the system, THz imaging of 30 FFPE samples have been carried out. Exemplary image is shown in FIG. 6A-6H.

THz imaging of the FFPE samples has shown the potential of Terahertz technology and the developed system to differentiate between benign and malignant tissues. The device has been able to detect the cancer margin up to mm precision, which is desirable in the standardized margin assessment protocol.

Fluorescence Imaging Results:

Auto-fluorescence imaging of FFPE tissue samples is measured at different wavelengths. The specimens are illuminated at various excitation wavelengths and images are captured with and without filters. The spatial distribution of tissue fluorescence at specific excitation wavelengths are recorded and the difference in fluorescence intensities between tumor and non-tumor is analyzed for cancer margin detection.

FIG. 7A-7H show exemplary fluorescence imaging of an FFPE sample for determining cancer and non-cancer regions.

Image Processing and AI

This disclosure proposes a new approach for the clinical classification of breast benign and malignant tissues. The method is based on measurement of Terahertz and fluorescence intensities from breast tissues. The capability of Terahertz radiation to differentiate between normal and abnormal tissue region are mainly due to free water content. Moreover, cancerous tissues exhibit greater free water content than normal tissues. However, origin of contrast is not only due to water content but also due to cancer cell density. That's because specific dielectric properties of the tissues in the low frequency region, were not observed in water dielectric profile. Since FFPE samples are dehydrated, the Terahertz contrast between healthy and malignant tissue is mainly due to the specific functional group and the cell density.

Present disclosure describes the image processing as below. Different FFPE samples such as complete tumor tissues, complete non-tumor tissues and tumor tissues with adjacent non-tumor tissues are utilized for the measurements. Both Terahertz and fluorescence images of each tissue are measured. In order to calculate the sensitivity and specificity of these results, from each of the FFPE samples, standard protocol, as explained under sample preparation was followed for the preparation of FFPE samples. The pathology image is obtained by slicing the FFPE tissues with 3-4 µm thickness and then stained with hematoxylin and eosin (H&E) to produce the histopathology image. The thickness of the embedded tissues varies from 2 to 3 mm which is not uniform due to the handling and shrinkage of the sample during formalin fixation for the pathologist analysis. The H&E slides are marked and benign and malignant tissues are demarked by an expert pathologist for the confirmation.

The Terahertz classified images, fluorescence images and the pathology images do not share the same coordinate system. Image registration is the process of migrating different images into one common coordinate system. Therefore, image registration is necessary to enable comparison between the data sets.

Effectively, the spatial resolution of pathology images, fluorescence images and Terahertz images are entirely different. In addition to that, the orientations of the tissue in all the images are expected to be different, as they are not acquired at the same angle. Hence, a simple pixel-by-pixel comparison is not possible. Prior to comparison, the images have to be resized and reoriented. The different steps that are followed to register the images with respect to each other are hereafter described.

Image Registration:

Contouring and ROI Extraction:

In order to extract the tissue area from the background and the paraffin area, the Region of Interest (ROI) is extracted by masking and determining the threshold value. The pathology image is converted to grayscale image and based on the grayscale intensity on the entire image; one grayscale threshold value may be decided. Based on the grayscale threshold intensity, masking is done in order to extract the ROI from the pathology image.

Similarly, to extract the tissue region of the fluorescence image from the paraffin embedded sample, a binary mask is created. As the shape of the tissue is not uniform in all the samples, lasso technique is used to crop the image by converting the RGB image to grayscale image.

Resizing:

As mentioned earlier, the spatial resolution of pathology image, fluorescence image and Terahertz image is different. Once the ROI is extracted from the pathology image, the image is resized according to the Terahertz image. Similarly, resizing of fluorescence image with the terahertz image is carried out in order to extract the features from both the images.

Lasso Masking

In order to train the artificial intelligence algorithm using terahertz and fluorescence data, the cancer and non-cancer regions are identified by overlapping the pathology image with the terahertz and fluorescence image.

In order to obtain the cancer region from the pathology image, lasso technique is used. Using lasso technique, freehand mask is created in order to segment the cancer region and non-cancer region.

Once both the regions are segmented from the pathology image, the masked region is overlapped with fluorescence and terahertz images.

Feature Extraction

Although the originally acquired signals contain raw input information, we do not typically use them as inputs in their original form. The raw signals contain significant redundancy with respect to the task, and the use of Machine Learning to analyze raw signals becomes inefficient due to the interfering effect of redundant components. Hence, first step is extraction of key features that better represent core information from the raw signals and use them as inputs of both the training and testing datasets. As such, Machine Learning learns a model that best describes a function from input features to targets in the training dataset.

Once cancer and non-cancer regions are segmented in the terahertz and pathology images, important features are extracted for the classification algorithm. As Terahertz image is obtained by raster scanning of the sample, terahertz spectra is obtained at each pixel of the image. The important features such as average intensity, peak intensity, area under the curve over a frequency range, Terahertz power etc. are extracted at each pixel.

In this disclosure, Principal Component Analysis (PCA) is used as a feature reduction technique.

Similarly, from the fluorescence images, the measurements are carried out at different excitation wavelengths such as 365 nm, 395 nm and 415 nm and emission wavelengths such as 415 nm, 470 nm, 525 nm and 630 nm. The average intensities at all twelve images are considered for the classification algorithm.

From both Terahertz and fluorescence data, PCA parameters are extracted and the machine learning algorithm is analyzed by combine Terahertz and fluorescence imaging results.

AI Module

Support vector machine (SVM) and random forest analysis have been carried out using both THz parameters and PCA parameters to classify benign and malignant tissue types.

All classification was performed to find the decision boundary between the two groups (tumor and normal tissues).

In this supervised learning, part of the data (70%) is used to train the classifier (training set), randomly selected and the rest of the data (30%) is used for testing data. A grid search using ten-fold cross-validation was conducted to find the optimal parameters by which the model can be trained properly. Ten-fold cross-validation has been carried out and misclassification rates have been verified for each combination.

Classification of THz Pulsed Data by Random Forest

Random forest is an ensemble learning model consisting of multiple decision trees, resulting in a more generalized model by averaging the learned results of multiple decision trees. As random forest uses only a decision tree, different training datasets are applied to each decision tree based on the bagging approach and each decision tree searches for the best feature element.

Machine Learning Classifier on Terahertz Measurements

Figure 8A:
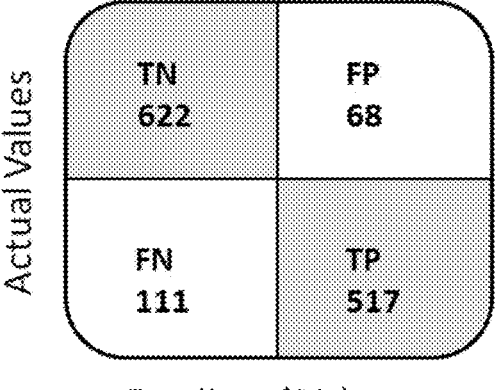
FIG. 8A-8C shows the confusion matrices utilizing multispectral results for determining breast cancer margin in real time.

More than thirty FFPE sample have been imaged using the setup. More than four thousand data sets are used for the classification. The Terahertz reflected spectra at each pixel is used as input data set for the classifier. PCA analysis, which is an unsupervised classifier, is carried out on the Terahertz dataset. These principal components are used as the input features to the classifier. In this analysis, the top ten principal components are used as input to the random forest classifier. The data set has been split into 70/30 in which 70% dataset is used to train the model and 30% to test the model. The confusion matrix on the THz testing data is shown in FIG. 8A.

It has been confirmed that more than 1100 data sets are classified properly and approximately 170 datasets are misclassified. The classification model has been analyzed more than ten times and the average sensitivity, specificity and accuracy is calculated. Random forest analysis on Terahertz results provides 85 to 88% accuracy, 80 to 85% sensitivity and 82 to 85% specificity.

Machine Learning Classifier on Fluorescence Measurements

Figure 8B:
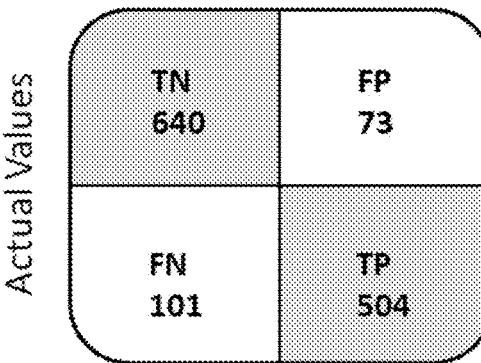

The autofluorescence imaging is carried out at different excitation and emission wavelengths as mentioned earlier. The average intensity at all twelve wavelengths are included in the algorithm and the most five important features are extracted based on the feature importance values. The principal components are extracted from these most important features. FIG. 8B also explains the Confusion Matrix from random forest analysis by utilizing Fluorescence measurement results.

The fluorescent measurement results confirmed that more than 1100 data sets are classified properly and approximately 170 datasets are misclassified. The classification model has been analyzed more than ten times and the average sensitivity, specificity and accuracy is calculated. Random forest analysis on fluorescence results provides 88 to 90% accuracy, 84% sensitivity and 83% specificity.

Combining Terahertz and Fluorescent Measurement Results

In order to combine both the measurement results, the fluorescence images are resized according to the Terahertz images so that numbers of data sets are equal in both the measurement techniques. The most important features form both Terahertz and fluorescence images are combined for the classification algorithm.

Figure 8C:
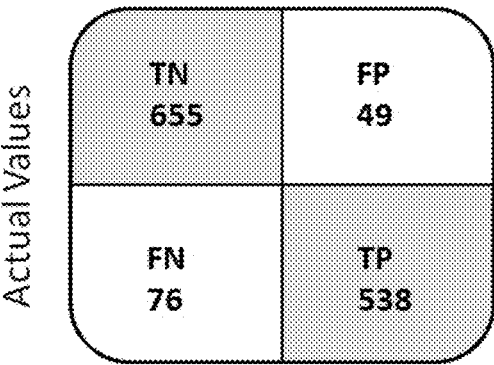

Combining both the techniques, the accuracy has been increased to 90 to 95%, sensitivity is 85 to 90% and the specificity is improved to 92 to 95%. Confusion Matrix by utilizing Terahertz and Fluorescence measurement results is also shown in FIG. 8C.

Thus, combining both the modalities improves the diagnostic accuracy of the results. Since, both the techniques are completely non-invasive and reagent free technology, may help the oncosurgeons to analyze the cancer margin much rapidly. It may help to differentiate the cancer and non-cancer tissues based on their structural difference, metabolic changes and the water content.

Advantages

The disclosure provides a system and device for detection of breast cancer margin with high accuracy ranging from 85-93%, specificity ranging from 90-95% and sensitivity up to 83-90%.

The detection method is rapid and real time which saves time and can be done in 40-60 min.

The detection of breast cancer margin can be done intraoperatively which helps oncosurgeons to take the decision accurately and immediately during the surgery.

The device may provide both Terahertz intensity and fluorescence intensity simultaneously with additional information.

The employed technique is non-invasive, non-ionizing and reagent-free technique which is highly beneficial for medical diagnostics.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet, including but not limited to PCT Application No. PCT/IN2022/050571 and Indian Patent App. No. 202141012592, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A multispectral imaging system for real time detection of breast cancer margin during a tumor resection surgery by combining terahertz and autofluorescence images, comprising;
   a sample holder mounted on a stepper motor, adapted to hold and move a tissue sample in Z-axis and X-axis directions to enable raster scan of the sample;
   an optical controller, configured to accommodate at least one laser source to provide an optical input;
   a housing, configured to accommodate optical components, wherein the optical components include:
      a terahertz module having a terahertz emitter antenna adapted to generate terahertz radiation from the received optical input, one or more lenses to guide the generated terahertz radiation to the sample and a terahertz detector to receive reflected terahertz signal from the sample;
      a fluorescence module configured to generate and pass fluorescence radiation through the sample and to receive emitted autofluorescence, wherein the fluorescence module comprises:
         an imaging module configured to provide at least one excitation wavelength in infrared/ultraviolet range using one or more multiwavelength excitation LED to illuminate the sample to emit autofluorescence;
         an image acquisition module having one or more emission filters of predetermined wavelength adapted to filter the emitted autofluorescence from the sample;
         a camera to detect the filtered autofluorescence and generate an image based on autofluorescence;
   an electronic control unit connected to the optical controller to supply power, wherein the electronic control unit is configured to provide bias to the terahertz emitter antenna and form terahertz image with data acquisition unit; and

a microcontroller connected to the electronic control unit, configured to display or to combine terahertz and autofluorescence images to determine breast cancer margin.

2. The system as claimed in claim 1, wherein a servo gear with a servo motor is employed for moving the emission filters.

3. The system as claimed in claim 1, wherein the microcontroller comprises a Graphical User Interface to display the processed images.

4. The system as claimed in claim 1, wherein at least one excitation wavelength is in the range of 300-500 nm.

5. The system as claimed in claim 1, wherein the predetermined wavelength of emission filters is 415 nm or 470 nm or 525 nm or 630 nm.

6. A method of real time detection of breast cancer margin during a tumor resection surgery using a multispectral imaging system as claimed in claim 1, the method comprising the steps of:
   providing the multispectral imaging system having a sample holder, an optical controller, a housing, an electronic control unit and a microcontroller, wherein the housing comprises a terahertz module with a terahertz emitter antenna, a terahertz detector antenna and a fluorescent module;
   providing and mounting a tissue sample onto the sample holder;
   generating optical input by at least one laser source in an optical controller;
   receiving the optical input in a terahertz module biased by an electronic control unit and guiding the generated terahertz radiation towards the sample;
   obtaining terahertz radiation from each pixel of the sample by terahertz detector antenna;
   generating fluorescence radiation in the fluorescence module and passing through the tissue sample to generate autofluorescence image;
   receiving reflected terahertz signal and autofluorescence response from the sample and capturing corresponding images;
   comparing and overlapping the obtained terahertz and autofluorescence images to corresponding stored histopathology images in the microcontroller; and
   segmenting cancer and noncancer regions, classifying and determining breast cancer margin by an artificial intelligence (AI) module.

7. The method as claimed in claim 6, wherein the method provides an improved breast cancer margin detection accuracy or specificity or sensitivity as compared to either the terahertz module or the fluorescence module alone.

8. The method as claimed in claim 6, wherein the AI module is configured for:
   capturing multispectral image data of an excised tissue sample;
   processing image data, resizing, analyzing and validating the preprocessed image data by overlapping image data with histopathology image;
   classifying the cancer and noncancer regions for each spectral image;
   combining spectral image validation data to form a feature set; and
   performing classification of the feature set by supervised vector machine or random forest machine learning model to obtain final classification with high sensitivity and specificity.

* * * * *